United States Patent [19]

Schwob

[11] 4,274,588
[45] Jun. 23, 1981

[54] STEAM DISPENSER, FOR DOMESTIC USE, FOR SKIN CARE

[75] Inventor: Pierre Schwob, Lyons, France

[73] Assignee: SEB S.A., Selongey, France

[21] Appl. No.: 69,984

[22] Filed: Aug. 27, 1979

[30] Foreign Application Priority Data

Jul. 10, 1979 [FR] France .............................. 79 17842

[51] Int. Cl.$^3$ .............................................. B05B 1/24
[52] U.S. Cl. .............................. 239/138; 222/146 HE
[58] Field of Search .............................. 239/136–139, 239/306, 308, 318; 222/146 R, 146 HA, 146 HS, 146 HE, 402.11, 402.13, 630; 219/272, 271; 251/231

[56] References Cited

U.S. PATENT DOCUMENTS

| 1,989,912 | 2/1935 | Brever | 239/138 |
| 1,994,407 | 3/1935 | Stone et al. | 239/138 |
| 2,000,628 | 5/1935 | White | 239/136 UX |
| 2,362,885 | 11/1944 | Clark et al. | 239/138 |
| 2,468,010 | 4/1949 | Duberstein | 239/138 X |
| 3,745,306 | 7/1973 | Naritomi | 219/272 |

FOREIGN PATENT DOCUMENTS 1568328  4/1969  France ..................................... 239/138

Primary Examiner—Robert B. Reeves
Assistant Examiner—Gene A. Church
Attorney, Agent, or Firm—Young & Thompson

[57] ABSTRACT

The steam dispenser comprises a steam generator 3 including an electric heating resistance 4 and connected to a dispensing nozzle 11, a reservoir 7 containing a lotion to be mixed with the steam dispensed by the nozzle 11.

A water feed chamber 15, having a water feed opening 18 is separated from the steam generator 3 by an electrically insulating wall 17 having a communication opening 20 closable by means of a valve 16.

The use of steam dispensers, for domestic use, for skin care.

4 Claims, 4 Drawing Figures

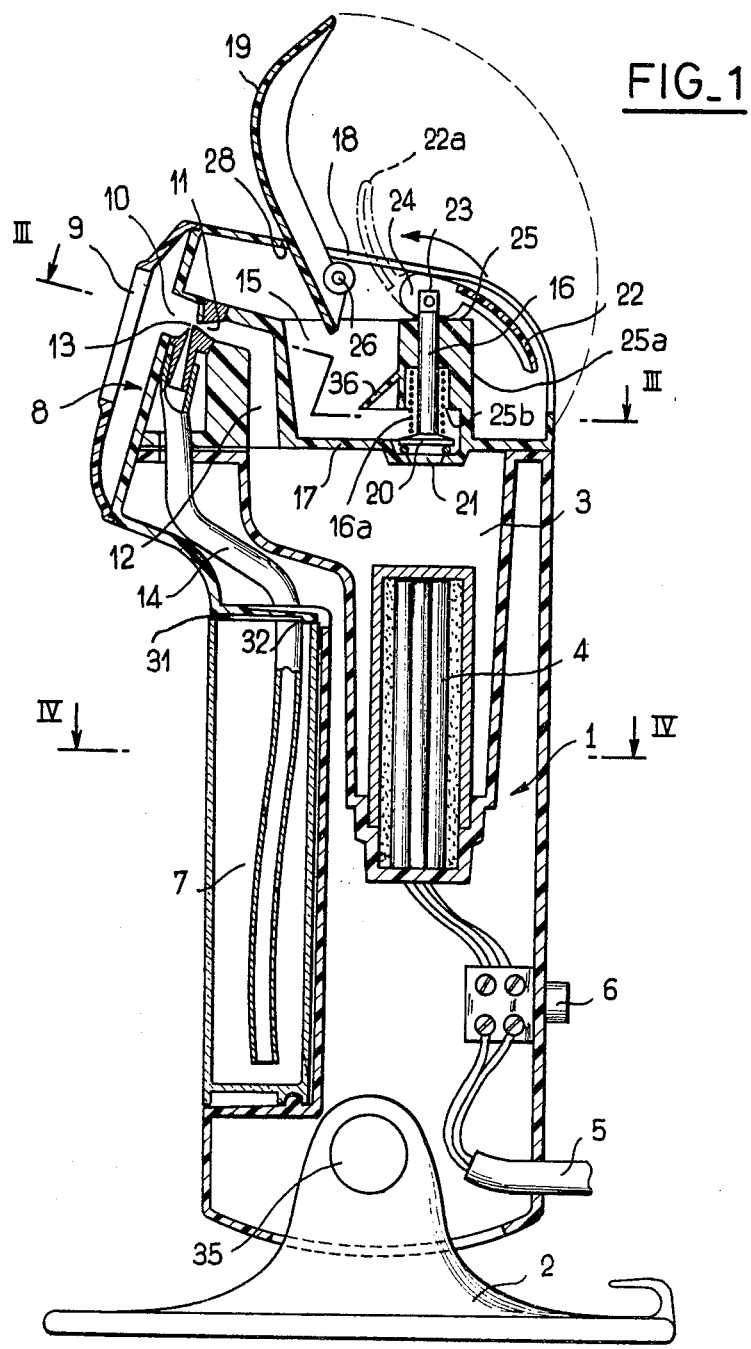

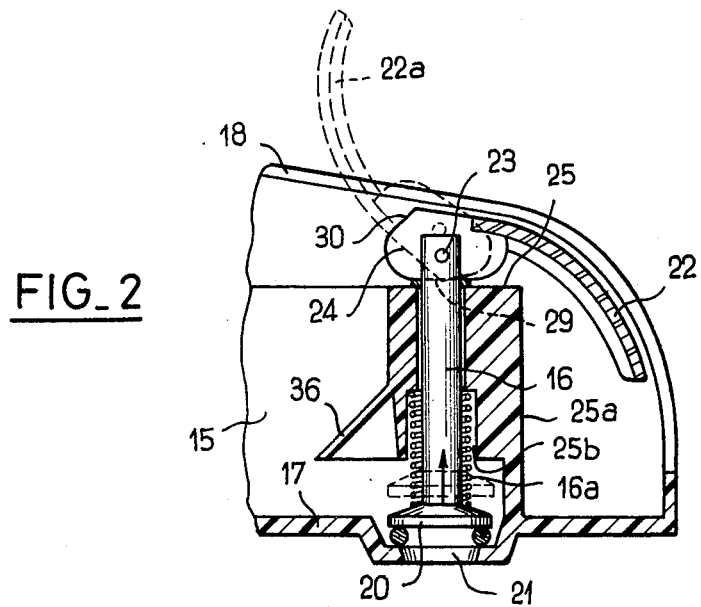
FIG_2
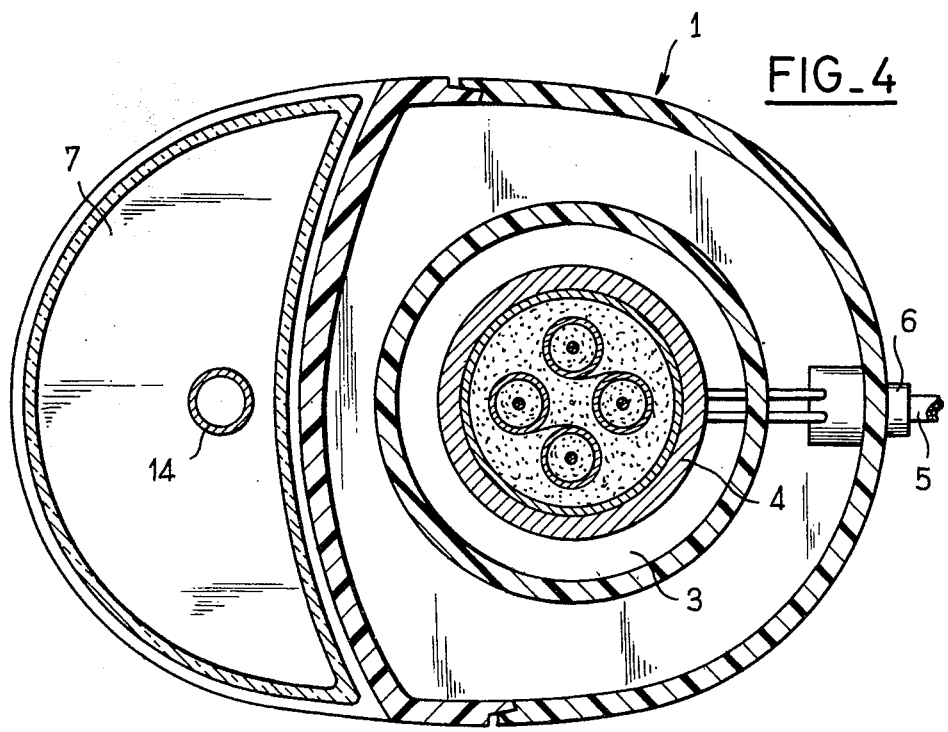
FIG_4

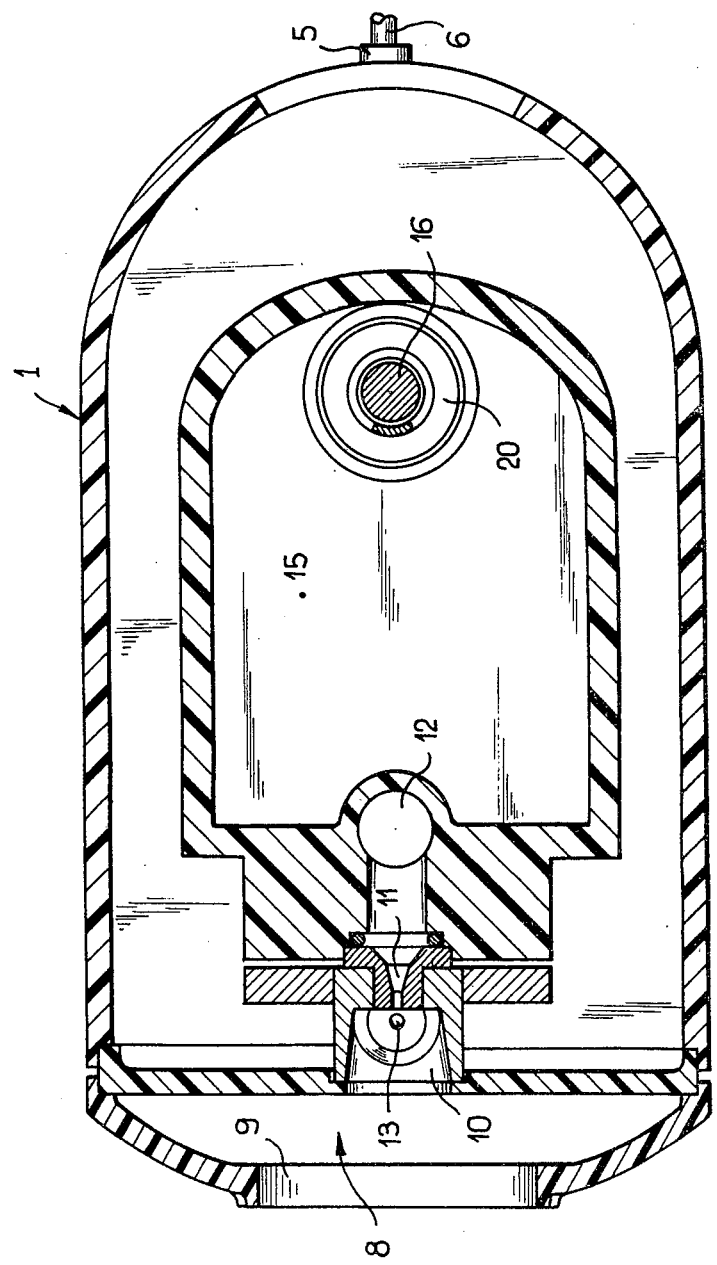
FIG_3

STEAM DISPENSER, FOR DOMESTIC USE, FOR SKIN CARE

The present invention relates to a steam dispenser, for domestic use, particularly for skin care and especially care of the face.

Professional dispensers are known comprising a steam generator of high capacity including an electric heating resistance and connected to a dispensing nozzle, and a reservoir containing a lotion to be mixed with the steam dispensed by the nozzle. This lotion may be a perfumed and/or disinfectant solution, or a solution including a cosmetic or pharmaceutical substance suitable to the treatment that one wishes to apply to the skin.

Because of their size and complexity, and thus their high price, such professional dispensers are not suited for domestic use.

The provision of a steam dispenser, for domestic use, is attended from the outset by great difficulties. In fact, for domestic use, it is necessary not only that the dispenser be of simple construction and easy and reliable to use, but especially that it satisfy the very strict safety rules imposed by legislation relating to domestic deivces. Ordinary electrical insulation, disposed between the heating resistance, the steam generator and the water contained in the latter, is not enough to satisfy the above-mentioned rules. In fact, if this insulation fails, the user may be electrocuted if he has direct access to the metallic or conductive parts of the steam generator. Moreover, the super-heated steam produced by a dispenser for domestic use must not, above all, in any case, give rise to burning of the skin, even if the user improperly operates it or makes some other error.

The invention has the particular object of overcoming all these difficulties.

The steam dispenser, for domestic use, according to the invention, comprises a steam generator including an electric heating resistance and connected to a dispensing nozzle and a reservoir containing a lotion to be mixed with the steam dispensed by the nozzle.

According to the invention, this dispenser is characterized in that it comprises a feed chamber for water having a water feed opening and separated from the steam generator by an electrically insulated wall having a communication opening closable by means of a valve.

Thanks to this feed chamber and the electrically insulating wall which separates the latter from the steam generator, the user cannot in any case have access to metallic or electrically conductive parts of the steam generator which are separated from the electrically charged parts by merely the usual electrical insulation.

According to an advantageous embodiment of the invention, the water feed opening of the feed chamber is provided with a cover and the operating means for the valve are disposed beneath this cover.

In this way, the user cannot open the valve until after the cover is opened, which he would not be likely to do when the dispenser is in operation. The risk of burns from steam is thus avoided.

According to a preferred embodiment of the invention, in the open position of the valve, the valve actuator means project from the opening of the feed chamber, thus preventing closing of the cover.

This arrangement improves the safety of the device. Thus, thanks to this arrangement, the user must first close the valve before closing the cover. He thus does not run the risk of being burned by a jet of steam escaping from the valve which was accidentally left open.

Preferably, the feed chamber has a volume smaller than or equal to that of the steam generator.

Thus, after opening the valve, all the water introduced in the feed chamber is emptied into the steam generator. In this way, after using the device, when the user opens the cover of the feed chamber, he cannot be burned by hot water which might have been left in the feed chamber.

Other features and advantages of the invention will become apparent from the following description.

In the accompanying drawings, given by way of nonlimitative example:

FIG. 1 is a longitudinal cross-sectional view of a dispenser embodying the invention, FIG. 2 is a cross-sectional view, on an enlarged scale, showing particularly the valve and its operator for the dispenser according to FIG. 1, FIG. 3 is a cross-sectional view on the line III—III of FIG. 1, omitting the base of the dispenser, FIG. 4 is a cross-sectional view on the line IV—IV of FIG. 1, omitting the base of the dispenser.

In the embodiment shown in the accompanying drawings, the steam dispenser according to the invention comprises a hollow body 1 of generally cylindrical shape, of a plastic material, secured to a base 2. Hollow body 1 includes a steam generator 3 including a heating element 4 having electrical resistances, connected to the electric supply cord 5. Heating element 4 is actuated by a switch 6.

The dispenser also comprises a reservoir 7 to contain a perfumed or disinfectant or cosmetic or pharmaceutical lotion, according to the treatment the user desires to apply.

The dispenser comprises, opposite its base 2, a dispensing head 8 having an opening 9 whose axis is inclined relative to the horizontal. This dispensing head 8 is adapted to be directed toward the portion of the user's skin to be treated.

To the rear of the opening 9 of the dispensing head 8 is disposed a dispensing chamber 10 into which opens, on the one hand, the outlet nozzle 11 which communicates by a conduit 12 with the steam generator 3, and on the other hand, the outlet nozzle 13 which is connected to the lotion reservoir 7 by means of a tube 14 of flexible material.

The axis of outlet nozzle 13 is substantially perpendicular to that the outlet nozzle 11 of the steam generator 3. Moreover, the outlet nozzle 13 is disposed slightly below the nozzle 11.

According to the invention, the dispenser has a water feed chamber 15 communicating with the interior of steam generator 3 by means of valve 16. This water feed chamber 15 is situated above steam generator 3, and is separated from the latter by an electrically insulating wall 17 of plastic material. This insulating wall 17 is mounted in sealed relationship on generator 3 by means of a joint (not shown). The feed chamber 15 has a water inlet opening 18 which is closed in operative position by a cover 19. This feed chamber 15, moreover, has a volume slightly less than that of the steam generator 3, these volumes being at most equal.

Valve 16 has actuating means which are disposed beneath cover 19 of feed chamber 15, when cover 19 is closed. Valve 16 comprises a head 20 which can tightly close an opening 21 provided in the wall 17 which separates feed chamber 15 from steam generator 3.

The actuating means of valve 16 comprise a pivoted lever 22 comprising, adjacent its pivot 23 relative to valve 16, a cam 24 that bears against a fixed surface 25 located on the interior of feed chamber 15. This fixed surface 25 is disposed at the top of a projection 25a which is traversed by valve 16 and which has a recess 25b containing a spring 16a which maintain valve 16 in closed position.

In FIG. 1, it will be seen that the pivot 26 of the cover 19 is located adjacent one of the edges 28 of water feed opening 18 of feed chamber 15. In the closed position of valve 16, shown in FIG. 1, lever 22 bearing cam 24 is swung toward the interior of reservoir 15, in a direction opposite pivot 26 of cover 19.

In the open position of valve 16, lever 22 is swung toward pivot 26 of cover 19 (see position 22a in phantom line in FIGS. 1 and 2). In this position, lever 22 closes a large part of feed opening 18 of feed chamber 15, which discourages the user from introducing water into reservoir 15 in the open position of valve 16. The stability of the open and closed positions of valve 16 is achieved by flats 29 and 30 respectively, provided on cam 24 of lever 22. These flats 29 and 30 are angularly related to each other by the same angle subtended between the open and closed positions of lever 22.

In the illustrated embodiment, lotion reservoir 7 is removably disposed in a lateral recess 31 of body 1 of the dispenser. This lotion reservoir 7 is maintained in position in recess 31 by means of resilient snap tabs 32 (see FIG. 1). This movement of the reservoir 7 is possible thanks to the flexibility of tube 14. This mounting permits refilling reservoir 7 with a lotion after the latter is used up.

Moreover, it will be seen in FIG. 1, that the body 1 of the dispenser is pivotally mounted on a pivot 35 on base 2, which permits directing the device toward the portion of the skin to be treated.

The operation of the steam dispenser just described is as follows:

Before any operation, one fills the device with water and with lotion. The water is introduced into the feed chamber 15, after opening cover 19. The lotion is introduced into the reservoir 7, after having withdrawn the latter sideways.

To introduce into the steam generator 3, the water contained in the feed chamber 15, one swings lever 22 toward position 22a, which raises valve 16 and initiates flow of the water into the vapor generator 3, through opening 21 of wall 17.

When all the water contained in the feed chamber 15 has flowed into steam generator 3, the valve 16 is closed by swinging lever 22 in a direction away from pivot 26 of cover 19.

The user is in no danger of forgetting to close valve 16, before closing cover 19, because the closure of the latter automatically causes swinging of lever 22 toward its closed position, thanks to the curved configuration of thses members. Locking means for lver 22 may also be provided to prevent closing the cover 19 when lever 22 is in open position.

The filling of steam generator 3 having been effected, heating of the water contained in the latter is effected by means of electrical resistor 4, by pressing on start button 6. Steam produced in generator 3 is dispensed by nozzle 11 toward the face of the user or any other part of the skin to be treated. The suction effected in recess 10 by this dispensing, sucks up the lotion contained in reservoir 7 which thus mixes with the dispensed steam.

While the device is turned on, the user is not in danger of electrocution, because he has no direct access to the steam generator in which the water is separated from the electrical resistor 4 only by conventional electrical insulation. The electrically insulating wall 17 thus provides the user with a double electrical security which permits a dispenser according to the invention to conform to the safety rules for devices for care of the face, skin and hair.

During heating of the water contained in the steam generator 3, the user is in no risk of being burned, even when opening cover 19, because the feed chamber 15 is completely empty, and the valve 16 is in its closed position.

Moreover, the user is not liable to introduce water directly into generator 3, which is to say by leaving valve 16 in open position, because in the open position of valve 16, the lever 22 closes the major portion of the water feed opening 18 of feed chamber 15.

Moreover, the user is in no danger of inadvertently opening the valve 16, when the device is heating, because the closed cover 19 prevents direct access to the lever 22 which actuates the valve 16.

Of course, the invention is not limited to the examples just described, and numerous modifications may be introduced therein, without departing from the scope of the invention.

The lotion reservoir 17 and the feed chamber 15 may be, partly or totally, transparent, and have graduations to indicate the level of water contained in these reservoirs. Similarly, the steam generator 3 may have a level indicator.

Steam generator 3 also comprise a safety valve in case of abnormal steam build-up due, for example, to blockage of the dispensing nozzle 11.

Valve 16 and lever 22 for actuating the latter may be replaced by other closure and actuating means, provided these means are disposed in the interior of the feed chamber 15, under the cover 19, thus making it impossible, for the user, to have direct access to the steam generator 3.

Flat 30 of cam 24 can be omitted. In this case, the open position of valve 16 is unstable, which provides added safety.

Safety may be further improved by providing on projection 25a an inclined wall 36 (see FIGS. 1 and 2), disposed between the feed opening 18 of feed chamber 15 and communication opening 21 of wall 17.

I claim:

1. A steam dispenser, for domestic use, for skin care, comprising a steam generator containing an electric heating resistance element and connected to a dispensing nozzle, a reservoir for a lotion to be mixed with steam dispensed by said nozzle, and a water feed chamber having an opening provided with a cover and separated from the steam generator by an electrically insulating wall provided with an opening closable by a valve, said valve having a steam cooperating with an articulated actuating lever which projects through the opening of the feed chamber and prevents closing of the cover when the valve is opened and closes the valve automatically when the cover of the feed chamber is closed.

2. Dispenser according to claim 1, wherein the valve has a stem and a head, the head cooperating with said opening in the wall, and the actuating means of the valve comprising an articulated lever having, in the vicinity of its pivot, a cam acting on the stem of the valve, against the action of a return spring.

3. Dispenser according to claim 2, the feed chamber comprising a cover pivoted on one of the edges of the water feed opening of the feed chamber, wherein in the closed position of the valve, the pivotal lever is swung toward the interior of the feed chamber, in a direction away from the pivot of the cover, and in the open position of the valve, the lever is swung toward the pivot of the cover.

4. Dispenser according to claim 2, wherein in the open position of the valve, the lever closes at least a part of the water feed opening of the feed chamber.

* * * * *